United States Patent [19]

Kiener

[11] Patent Number: 5,242,816
[45] Date of Patent: Sep. 7, 1993

[54] MICROBIOLOGICAL OXIDATION OF ALKYL GROUPS IN HETEROCYCLES

[75] Inventor: Andreas Kiener, Visp, Switzerland

[73] Assignee: Lonza Ltd., Gampel/Valais, Switzerland

[21] Appl. No.: 725,477

[22] Filed: Jul. 3, 1991

[30] Foreign Application Priority Data

Jul. 10, 1990 [CH] Switzerland .......... 2298/90
Sep. 20, 1990 [CH] Switzerland .......... 3047/90

[51] Int. Cl.⁵ .......... C12P 17/10; C12P 17/12; C12P 17/02
[52] U.S. Cl. .......... 435/122; 435/121; 435/253.3; 435/874; 435/117; 435/135; 435/123; 435/130; 435/136
[58] Field of Search .......... 435/121, 253.3, 122, 435/135, 117, 874, 123, 136, 130

[56] References Cited

FOREIGN PATENT DOCUMENTS 0274146 of 1987 European Pat. Off.
3822595 of 1989 Fed. Rep. of Germany.
2206578 of 1989 United Kingdom.

OTHER PUBLICATIONS

Fukuda et al., Agric. Biol. Chem., 53 (12), (1989), pp. 3293 to 3299.
Raymond R. L., Process Biochemistry (1969), pp. 71 to 74.
Patent Abstracts of Japan, C Field, vol. 9, No. 260, (Oct. 17, 1985), p. 151 C 398, first abstract.
Kulla et al., Arch. Microbiol., 135, (1983) pp. 1 to 7.
Witholt et al., Tibtech, vol. 8, (1990), pp. 46 to 52.
Ullmann, (1983), vol. 23, p. 219.
Grund et al., J. Bacteriol., 123, (1975), pp. 546 to 556.

Primary Examiner—David M. Naff
Assistant Examiner—L. Blaine Lankford
Attorney, Agent, or Firm—Fisher, Christen & Sabol

[57] ABSTRACT

A microbiological process for the terminal oxidation of alkyl groups in 5- or 6-ring heterocycles which are substituted with at least one alkyl group with more than 2 carbon atoms to carboxylic acids. The reaction takes place by alkane- and/or alkanol-utilizing microorganisms 4 Claims, No Drawings

MICROBIOLOGICAL OXIDATION OF ALKYL GROUPS IN HETEROCYCLES

BACKGROUND OF THE INVENTION

1. Field of the Invention

The invention relates to a novel microbiological process for the terminal oxidation of alkyl groups of heterocycles to carboxylic acid.

2. Background Art

Thorough studies for the microbiological oxidation of alkyl groups in aliphatic hydrocarbons have been performed, among others, with the microorganism strain *Pseudomonas oleovorans*.

Regarding *Pseudomonas oleovorans* ATCC 8062 and ATCC 29347, it is known that the biochemical oxidation of alkanes proceeds in three steps to the corresponding acid. By the action of the alkane hydroxylase complex, first the corresponding alcohol results, which then in two steps, catalyzed by an alcohol dehydrogenase and an aldehyde dehydrogenase, is converted to the acid.

In this strain the genes, which are responsible for the enzymes of this oxidation, are on the plasmid OCT [Witholt et al., TIBTECH, Vol. 8, (1990), pp. 46 to 52].

The microbiological oxidation of alkyl groups to the corresponding acids by *Pseudomonas oleovorans* so far has been described only in compound with linearly saturated alkyl groups with 6 to 12 carbon atoms and with ethyl benzene [Fukuda et al., Agric. Biol. Chem. 53 (12), (1989), pp. 3293 to 3299].

The oxidation of alkyl-substituted cyclic aromatic or saturated hydrocarbons to the corresponding carboxylic acid with alkane-utilizing microorganisms such as *Rhodococcus*, *Mycobacterium* and *Pseudomonas* is described by Raymond, R. L., Process Biochemistry (1969), pp. 71 to 74.

The disadvantages of this process are that the reaction is not specific for alkyl groups with more than two carbon atoms, that ring cleavages can also occur and also that methyl groups in aromatic hydrocarbon compounds are oxidized.

BROAD DESCRIPTION OF THE INVENTION

The main object of the invention is to provide a simple and one-step process for the microbiological alkyl group oxidation of heterocycles, with which the corresponding acids can be isolated in good yield and purity and the aromatic or saturated heterocycle is not cleaved. Other objects and advantages of the invention are set out herein or are obvious herefrom to one ordinarily skilled in the art.

The objects and advantages of the invention are achieved by the process of the invention.

The invention involves a microbiological process for the terminal oxidation of alkyl groups of heterocycles to carboxylic acid. As the substrate, a 5- or 6-ring heterocycle, substituted with at least one alkyl group with at least 2 carbon atoms, by alkane- and/or alkanol-utilizing microorganisms is reacted to the corresponding carboxylic acid, and the resultant carboxylic acid is not further catabolized.

The carboxylic acid derivatives resultant from the invention process can, for example, be used as intermediate products for pharmaceuticals, such as, thiophene-2-acetic acid (2-thienylacetic acid) for the synthesis of penicillin/cephalosporin antibiotics [Ullmann, (1983), Vol. 23, p. 219].

DETAILED DESCRIPTION OF THE INVENTION

As substrates for the reaction according to the invention, 5- or 6-ring heterocycles are used which are ring-substituted with at least one alkyl group having at least 2 C atoms, suitably 2 to 6 C atoms, preferably 2 C atoms. Suitably such 5- or 6-ring heterocycles exhibit an oxygen, nitrogen or sulfur atom as the heteroatom (although the heterocycle can have more than one heterocycle). Preferably the 6-ring heterocycles are those with a nitrogen heteroatom. Suitable representatives of the 5-ring heterocycles are thiophenes, furans, pyrroles, thiazoles, pyrazoles or imidazoles. Especially, 2-ethylthiophene or 2-ethylfuran is used as the 5-ring heterocycle. Suitable representatives of the 6-ring heterocycles are pyridines, pyrimidines, pyrizines or pyridazines. Especially, 3-ethylpyridine, 2-ethylpyrazine or 5-ethyl-2-methylpyridine is used as the 6-ring heterocycle.

Suitably the enzymes of the alkane- and/or alkanol-utilizing microorganisms are induced. The concept alkanes or alkanols also comprise substituted alkanes or alkanols (alkylated cyclic compounds) such as, phenyl-substituted ethane (ethylbenzene).

The enzyme induction can be performed both with compounds, which serve as the carbon source and energy source for the microorganism, such as, alkanes, alkanols, alkylated cyclic compounds, for example, octane, octanol, dodecane, dodecanol, hexane, hexanol and ethylbenzene, and with compounds which do not serve as the carbon source and energy source for the microorganism, for example, dicyclopropyl ketone, dicyclopropyl methanol and diethoxyethane, which are already described in Grund et al., J. Bacteriol., 123, (1975), pp. 546 to 556. Preferably, the enzyme induction of *Pseudomonas oleovorans* is performed with n-octane, of *Candida tropicalis* with n-hexadecane and of *Rhodococcus rhodochrous* with n-decane.

Usually the feeding of the compounds used for the induction is stopped during the reaction of the substrate. But the reaction of the substrate can also take place even in the presence of the enzyme inducer. Preferably the feeding of the compounds used for induction is stopped during the reaction of the substrate either by the stopping of the feeding or by the centrifuging off of the cells.

The reaction can be performed with alkane- and/or alkanol-utilizing microorganisms, such as, with those of the genus Pseudomonas, with yeasts of the genus Candida and with microorganisms of the genus Rhodococcus. Mutants of these microorganisms as well as other microorganisms are also suitable for the process, into which the genetic information necessary for the reaction was introduced either by conjugation or by genetic engineering methods, and thus form the effective enzymes for the reaction.

Alkane-utilizing microorganism strains *Pseudomonas oleovorans* with the designation ATCC 8062 or ATCC 29347, yeasts of the species *Candida tropicalis* with the designation ATCC 32113 and *Rhodococcus rhodochrous* with the designation ATCC 19067 can be used as microorganisms, preferably *Pseudomonas oleovorans* with the designation ATCC 29347. The microorganism strains *Pseudomonas oleovorans* ATCC 8062 or ATCC 29347 and *Rhodococcus rhodochrous* ATCC 19067, as well as yeasts of the genus *Candida tropicalis* ATCC 32113, have been deposited at the American Type Culture Collection, 12301 Parklawn Drive, Rockville, Md. 20852, USA.

Such strains grow with alkanes, alkanols or with alkylated cyclic compounds in a mineral salt medium [Kulla et al., Arch. Microbiol. 135, (1983), pp. 1 to 7], or in a complex medium ["Nutrient Broth Nr. 2," Oxoid Ltd., England].

Before the addition of the substrate, the cells are cultivated in the usual way and then the reaction of the substrate is performed at an optical density of 1 to 200 at 650 nm in the culture medium, preferably at an optical density of 5 to 100 at 650 nm. The reaction can take place either with one-time or continuous addition of substrate so that the substrate concentration in the culture medium does not exceed 20 percent (w/v). The term (w/v) is an abbreviation for weight by volume. Preferably, the addition of substrate takes place so that the substrate concentration in the culture medium does not exceed 5 percent (w/v), especially that the substrate concentration in the culture medium does not exceed 1 percent (w/v).

The reaction suitably is performed in a pH range of 4 to 11, preferably of 6 to 10. The reaction is usually performed at a temperature of 15° to 50° C., preferably at a temperature of 25° to 40° C. The reaction is suitably performed in a period of 1 hour to several days; preferably the reaction is performed with a continuous process over several days.

After the reaction is ended, the corresponding acids can be isolated in a known way.

EXAMPLE 1

(2-Methylpyridine-5-Acetic Acid)

*Pseudomonas oleovorans* ATCC 29347 was cultivated in a mineral salt medium [Kulla et al.. Arch. Microbiol. 135, (1983), pp. 1 to 7] with n-octane as the sole carbon and energy source at 30° and a pH of 7. Then the cells were washed twice with the same mineral salt medium and an optical density of 10 at 650 nm in 100 ml of mineral salt medium was set. To this cell suspension was added 1 mmol of 5-ethyl-2-methylpyridine, which corresponds to a substrate concentration of 0.12 percent (w/v). After an incubation of 16 hours at 30° C., in the absence of n-octane, 0.5 mmol of 2-methylpyridine-5-acetic acid corresponding to a yield of 50 percent, relative to the ethylmethylpyridine used, was obtained. Under these conditions no oxidation of the methyl group in the ethylmethylpyridine could be detected.

Examples 2 to 5 were performed according to Example 1 with an amount of 1 mmol of substrate per 100 ml of cell suspension and are summarized in Table 1.

TABLE 1

| Example | Concentration of substrate in % (w/v) in culture medium | Reaction time in hours | End Product | Yield in % (w/v) |
|---|---|---|---|---|
| 2 3-ethyl-pyridine | 0.108 | 16 | pyridine-3-acetic acid | 20 |
| 3 2-ethyl-pyrazine | 0.109 | 16 | pyrazine-2-acetic acid | 20 |
| 4 2-ethyl-thiophene | 0.113 | 16 | thiophene-2-acetic acid | 20 |
| 5 2-ethyl furan | 0.097 | 16 | furan-2-acetic acid | 20 |

What is claimed is:

1. A microbiological process for terminal oxidation of alkyl groups to carboxylic acids which comprises:
   (a) converting an aromatic 5- or 6-membered heterocyclic compound with an ethyl group sustituent, wherein said compound contains one or more heteroatoms selected from the group consisting of oxygen, nitrogen or sulfur, into the compound's corresponding carboxylic acid by oxidizing said ethyl group without further catabolizing said carboxylic acid, by culturing *Pseudomonas oleovorans* DSM 6827 or a mutant which retains the capability of said terminal oxidation in the presence of said aromatic 5- or 6-membered hetrocyclic compound, and
   (b) recovering said carboxylic acid.

2. Process according to claim 1 wherein the reaction is performed either with one-time or continuous addition of the substrate so that the substrate concentration in the culture medium does not exceed 20 percent (w/v).

3. Process according to claim 1 wherein the reaction is performed at a pH of 4 to 11.

4. Process according to claim 1 wherein the reaction is performed at a temperature of 15° to 50° C.

* * * * *